(12) United States Patent
Fujita et al.

(10) Patent No.: US 6,433,201 B2
(45) Date of Patent: Aug. 13, 2002

(54) PROCESS FOR SEPARATING AND PURIFYING EICOSAPENTAENOIC ACID OR ITS ESTER

(75) Inventors: Shiro Fujita, Saitama-ken; Yuji Asami; Toru Ikeda, both of Ueda, all of (JP)

(73) Assignee: Nisshin Flour Milling Co., Ltd., Tokyo (JP)

( * ) Notice: Subject to any disclaimer, the term of this patent is extended or adjusted under 35 U.S.C. 154(b) by 0 days.

(21) Appl. No.: 09/779,618

(22) Filed: Feb. 9, 2001

(30) Foreign Application Priority Data

Feb. 14, 2000 (JP) ........................................ 2000-035140

(51) Int. Cl.⁷ ................................................ C11B 3/10
(52) U.S. Cl. ........................................ 554/191; 584/193
(58) Field of Search ................................. 584/191, 193

(56) References Cited

FOREIGN PATENT DOCUMENTS

| EP | 0 610 506 | 8/1994 |
|----|-----------|--------|
| EP | 0 712 651 | 5/1996 |
| JP | 5-222932  | 8/1993 |
| JP | 9-151390  | 6/1997 |
| SU | 973128    | 11/1982 |

*Primary Examiner*—Deborah D. Carr
(74) *Attorney, Agent, or Firm*—Oblon, Spivak, McClelland, Maier & Neustadt, P.C.

(57) ABSTRACT

Eicosapentaenoic acid or its ester is separated and purified from a mixture containing a highly unsaturated fatty acid or its ester effectively at low cost by a process, which comprises developing the mixture by a mixed solvent of an ether solvent and a hydrocarbon solvent, using a column filled with a silica gel having a particle diameter of 1–100 micrometers.

4 Claims, No Drawings

PROCESS FOR SEPARATING AND PURIFYING EICOSAPENTAENOIC ACID OR ITS ESTER

FIELD OF THE INVENTION

This invention relates to a process for purifying a highly unsaturated fatty acid or its ester. More particularly, the invention relates to a process for purifying eicosapentaenoic acid or its ester from a mixture containing the highly unsaturated fatty acid or its ester, by a silica gel column chromatography.

BACKGROUND OF THE INVENTION

Highly unsaturated fatty acids or their esters such as eicosapentaenoic acid (hereafter called "EPA") and docosahexaenoic acid (hereafter called "DHA") contained in fish oil such as sardine oil have been used in the field of drugs and health foods, since they have a pharmacological effect in vivo and are effective against diseases such as arteriosclerosis obliterans and hyperlipemia.

Known processes for the purification of these unsaturated fatty acids include a urea-addition process, a precision distillation process, a column chromatography process and a supercritical fluid extraction process. These processes have been used singly or in combination for purifying highly unsaturated fatty acids.

However, the urea-addition process is not satisfactory as a purification process for removing eicosatetraenoic acid (hereafter called "ETA") or its ester, because of its being poor in urea-adduct forming ability. The precision distillation process needs an operation at high temperature, and may easily cause denaturation by polymerization or isomerization. In the purification of EPA or its ester, the process has a great difficulty in removing ETA or its ester, because ETA and EPA have the same carbon numbers and make a small difference in boiling point. Further, since the supercritical fluid extraction process deals with high-pressure fluid, it has a difficulty in installation of equipment and it is unsuitable for mass separation and purification on an industrial scale.

As a process for the purification of highly unsaturated fatty acids using the column chromatography method, Japanese Patent Kokai 5-222392 discloses a combination of precision distillation and reverse phase partition chromatography using a silica gel on which an octadecyl group is held. Further, Japanese Patent Kokai 9-151390 discloses a purification process using a carrier having a silver salt carried on silica gel. These purification processes can separate and purify EPA and its ester from mixtures of highly unsaturated fatty acids. The former process is excellent in the separation and purification, but it has the problem that the cost of filler becomes high because the octadecyl group is held on the silica gel surface. The latter process has the problem that the cost is high due to use of the silver salt, that the method for the preparation of the carrier carrying the silver salt is complicated, that the extraction operation is complicated with repeated agitation and filtration, and that the product may be contaminated with a silver compound by using a particular solvent.

Usually, ETA and its ester are contained in the raw material of EPA and its ester. However, ETA and its ester are impurities very difficult to separate and remove in the purification of EPA and its ester, as mentioned above.

Thus, there has been a demand for a process for the purification of eicosapentaenoic acid or its ester, by which the problems encountered in the prior art can be overcome and the contents of ETA and its ester can be remarkably reduced by selectively removing impurities.

SUMMARY OF THE INVENTION

Accordingly, an object of the present invention is to provide a process for selectively separating and purifying eicosapentaenoic acid or its ester effectively at low cost.

A further object of the present invention is to provide a process for selectively separating and removing ETA or its ester by a normal phase column chromatography using the silica gel under a specific condition.

The present invention provides a process for separating and purifying eicosapentaenoic acid or its ester from a mixture containing a highly unsaturated fatty acid or its ester, which comprises developing the mixture containing the highly unsaturated fatty acid or its ester with a mixed solvent of an ether solvent and a hydrocarbon solvent, using a column filled with a silica gel having a particle diameter of 1 to 100 micrometers.

DETAILED DESCRIPTION OF THE INVENTION

In this process, the silica gel used as a filler of the column is required to have a particle diameter in the range of 1–100 micrometers. If the silica gel of small particle diameter is used, pressure loss will become large, but the amount of raw material loaded and the purifying capability will be increased due to its increased surface area. On the other hand, if the silica gel of large particle diameter is used, pressure loss will become small, but the amount of raw material loaded and the purifying capability will be reduced. Thus, it is required to choose the silica gel of suitable particle diameter in view of the amount of raw material loaded and purifying capability. For the selective separation of ETA or its ester, it is preferable to use the silica gel providing small pressure loss and having as large a specific surface area as possible. In the present invention, the form of silica gel may be spherical or fragment as far as the silica gel has the above-defined particle diameter, but spherical form is preferable. In addition, it is preferable to use porous silica gel having a pore size of not less than $4 \times 10^{-3}$ micrometers.

The amount of this silica gel used varies depending on the quantity of raw material to be processed and/or size of a column, etc., but it is usually within the range of 5–50 grams, preferably 10–40 grams per gram of raw material, i.e., the mixture comprising the highly unsaturated fatty acid or its ester.

In the present process, the mixture containing the highly unsaturated fatty acid or its ester is charged in the column filled with silica gel, and then developed with an organic solvent serving as a developing solvent. As the developing solvent, a mixed solvent with the highest purifying capability can be selected by varying the polarity of solvent. According to the present invention, the mixed solvent of a hydrocarbon solvent and an ether solvent is advantageous for the separation and purification of eicosapentaenoic acid or its ester.

The hydrocarbon solvents in the mixed solvent can include, but are not limited to, hydrocarbons of 5–8 carbons, preferably alkane hydrocarbons, for example, n-pentane, n-hexane, n-heptane and n-octane. The ether solvents can include, but are not limited to, dialkyl ethers, for example, diisopropyl ether, diethyl ether and methyl tert-butyl ether. In the present process, the developing solvent can be used in any combination of the hydrocarbon solvent and the ether solvent, but a mixed solvent of n-hexane (hereafter called "n-Hex") and diisopropyl ether (hereafter called "IPE") is especially preferable. A mixing ratio of these solvents can be suitably decided so as to provide optimum conditions for the purification of the desired EPA or its ester. For a mixed solvent of n-Hex and IPE, for example, the mixing ratio is a volume ratio of n-Hex:IPE=90-99:10-1, preferably 95-99:5-1.

In the preferred embodiment of the present invention, eicosapentaenoic acid or its ester can be separated from the mixture of the highly unsaturated fatty acid or its ester by a column chromatography, which comprises developing said mixture with a mixed solvent of n-Hex and IPE as a developing solvent, using a column filled with silica gel having a particle diameter of 1–100 micrometers, at a linear velocity of 1–10 cm/min.

From another viewpoint, the present invention relates to a process for selectively removing ETA or its ester from a mixture comprising a highly unsaturated fatty acid or its ester containing eicosatetraenoic acid (ETA) or its ester, by the above-described column chromatography.

The column used in the process of the present invention is prepared by suspending silica gel in an organic solvent to slurry it, filling the slurried silica gel in a medium pressure column and flowing an organic solvent about 1–10 times the volume of the column to stabilize the column. A preferable organic solvent used when filling silica gel in slurry is acetone. It is preferable that an organic solvent used in the stabilization of column is the same as the developing solvent used in the purification.

The optimum amount of the mixture containing the highly unsaturated fatty acid or its ester which should be charged in the column can be varied depending on the composition ratio of each fatty acid in the raw material, but it is in the range of 2 to 20% by weight, preferably 3 to 15% by weight, based on the weight of silica gel in the column. Preferably, the raw material, i.e., the mixture containing the highly unsaturated fatty acid or its ester is dissolved in a developing solvent at most 5 times, e.g., twice the weight of the mixture, and thereafter this solution is flowed through the column.

For the column used in the process of the invention, preferable is a medium pressure column with the column length diameter ratio of 2 or more and the theoretical plate number of 15000–20000 plates/m. The pressure resistance of column may be in the range of 1–6 MPa, depending on the length and the linear velocity of column. The column is preferably operated at 10–30° C., e.g., at room temperature. In the separation of ETA or its ester, it is preferable that the mixture of raw material is developed while applying the pressure so as to provide a linear velocity of 1–10 cm/min in the column.

The mixture containing the highly unsaturated fatty acid or its ester used as a raw material in the present process can be obtained from fish oils extracted from mackerels, sardines, codfishes, etc., but is not limited especially. This raw material mixture contains ETA, EPA, DHA and other components such as fatty acids of less than 20 carbons.

The invention is further illustrated by the following non-limiting examples and comparative examples.

EXAMPLE 1

(1) 39.2 g of spherical silica gel having an average particle diameter of 20 micrometers (manufactured by Soken Chemical & Engineering Co., Ltd.) were slurried with acetone and this slurry was filled under pressure in a stainless steel medium pressure column (20 mm in inside diameter×250 mm in length). Then, a mixed solvent (a volume ratio of IPE:n-Hex 3.2:96.8) 3.4 times the volume of the column was flowed to stabilize the column.

(2) The composition of the highly unsaturated fatty acid used as a raw material in this example is shown in the following Table 1. The highly unsaturated fatty acid in the raw material was subjected to ethyl esterification beforehand.

2.0 g of this raw material were dissolved in 4 ml of a mixed solvent (a volume ratio of IPE:n-Hex=3.2:96.8) and this solution was flowed into the column as prepared in (1).

First, the column was developed by 198 ml of the mixed solvent at a linear velocity of 7.0 cm/min, and the resultant effluent was condensed under reduced pressure in an evaporator, thus giving 0.23 g of oil as the first effluent fraction with the composition shown in the following Table 2.

Second, the column was developed by 7.4 ml of the mixed solvent at a linear velocity of 7.0 cm/min, and the resultant effluent was condensed under reduced pressure in an evaporator, thus giving 0.24 g of oil as the second effluent fraction with the composition shown in Table 2.

Third, the column was developed by 278.6 ml of the mixed solvent at a linear velocity of 7.0 cm/min, and the resultant effluent was condensed under reduced pressure in an evaporator, thus giving 1.48 g of oil as the third effluent fraction with the composition shown in Table 2.

Finally, the column was developed by 117.8 ml of acetone at a linear velocity of 7.0 cm/min, and the resultant effluent was condensed under reduced pressure in an evaporator, thus giving 0.06 g of oil as the fourth effluent fraction, with the composition shown in Table 2.

1.48 g of the oil obtained as the third effluent fraction was further subjected to high-vacuum precision distillation using a packed column type precision distillation tower having a theoretical plate number of 8 under the conditions: a degree of vacuum of not more than 0.02 mm Hg at the top of the tower, a degree of vacuum of not more than 2.0 mm Hg at the bottom of the tower and an average distillation temperature of 165–210° C. 1.18 g of oil having the composition shown in Table 3 was obtained.

The gas chromatograph used in the analysis was GC-17A Gas Chromatograph manufactured by Shimadzu Corporation.

The column condition is shown below.
Column: 0.25 mm (inside diameter)×30 m (length)
 (Trade name: DB-WAX manufactured by J&W)
Detector: FID
Column temperature: 210° C.
Inlet temperature: 250° C.
Detector temperature: 260° C.
Carrier gas: helium
Flow rate: adjusted so as to retain EPA ethyl ester for about 20 minutes.

The composition of the fatty acids in the raw material used in Example 1 is shown in Table 1.

TABLE 1

|  | Content of ethyl ester of each fatty acid (%) | | | |
| --- | --- | --- | --- | --- |
|  | ETA | EPA | DHA | Others |
| Raw material | 4.20 | 73.48 | 11.65 | 10.67 |

As a result of the chromatography in Example 1, the yield and the composition of each effluent are shown in Table 2.

TABLE 2

| | Yield (%) | Content of ethyl ester of each fatty acid (%) | | | |
| --- | --- | --- | --- | --- | --- |
| | | ETA | EPA | DHA | Others |
| First effluent fraction | 11.2 | 32.52 | 20.27 | 10.60 | 36.61 |
| Second effluent fraction | 11.8 | 5.69 | 68.53 | 17.10 | 8.68 |
| Third effluent fraction | 74.1 | 0.95 | 80.32 | 10.28 | 8.45 |
| Fourth effluent fraction | 3.0 | 1.30 | 66.18 | 9.56 | 22.96 |

The yield and the composition of the oil obtained by distillation of the third effluent fraction in Example 1 are shown in Table 3.

TABLE 3

| | Yield (%) | Content of ethyl ester of each fatty acid (%) | | | |
| --- | --- | --- | --- | --- | --- |
| | | ETA | EPA | DHA | Others |
| Product purified by distillation | 79.7 | 1.34 | 98.31 | 0.0 | 0.35 |

The result in Example 1 shows that ETA or its ester contained before purification was largely reduced by the process of the present invention and also that EPA of high purity of 98% or more could be obtained in the subsequent purification process by distillation.

COMPARATIVE EXAMPLE 1

(1) 39.2 g of spherical silica gel having an average particle diameter of 110 micrometers (manufactured by Fuji Silysia Chemical Ltd.) were slurried with acetone and this slurry was filled under pressure in the same medium pressure column as used in Example 1. Then, a mixed solvent (a volume ratio of IPE:n-Hex=3.2:96.8) 3.4 times the volume of the column was flowed to stabilize the column.

(2) 2.0 g of the same highly unsaturated fatty acid mixture as used in Example 1 were dissolved in 4 ml of the mixed solvent (a volume ratio of IPE:n-Hex=3.2:96.8) and this solution was flowed into the column as prepared in (1).

First, the column was developed by 198 ml of the mixed solvent at a linear velocity of 7.0 cm/min, and the resultant effluent was condensed under reduced pressure in an evaporator, thus giving 1.61 g of oil as the first effluent fraction with the composition shown in the following Table 4.

Second, the column was developed by 7.4 ml of the mixed solvent at a linear velocity of 7.0 cm/min, and the resultant effluent was condensed under reduced pressure in an evaporator, thus giving 0.22 g of oil as the second effluent fraction with the composition shown in Table 4.

Third, the column was developed by 278.6 ml of the mixed solvent at a linear velocity of 7.0 cm/min, and the resultant effluent was condensed under reduced pressure in an evaporator, thus giving 0.05 g of oil as the third effluent fraction with the composition shown in Table 4.

Finally, the column was developed by 117.8 ml of acetone at a linear velocity of 7.0 cm/min, and the resultant effluent was condensed under reduced pressure in an evaporator, thus giving 0.03 g of oil as the fourth effluent fraction with the composition shown in Table 4.

TABLE 4

| | Yield (%) | Content of ethyl ester of each fatty acid (%) | | | |
| --- | --- | --- | --- | --- | --- |
| | | ETA | EPA | DHA | Others |
| First effluent fraction | 80.5 | 4.70 | 72.05 | 11.72 | 11.53 |
| Second effluent fraction | 11.0 | 1.43 | 79.92 | 10.79 | 7.86 |
| Third effluent fraction | 2.5 | 1.98 | 79.55 | 10.78 | 7.69 |
| Fourth effluent fraction | 1.5 | 1.70 | 29.73 | 5.02 | 63.55 |

The result in Comparative Example 1 shows that ETA or its ester was insufficiently separated by using the silica gel of large particle diameter and also that the yields of the resultant second and third effluent fractions were extremely low. High-vacuum precision distillation of the oil in these effluent fractions could not result in EPA of 98% or more purity.

EXAMPLE 2

(1) 39.2 g of spherical silica gel having an average particle diameter of 40 micrometers (manufactured by Soken Chemical & Engineering Co., Ltd.) were slurried with acetone and this slurry was filled under pressure in the same medium pressure column as used in Example 1. Then, a mixed solvent (a volume ratio of IPE:n-Hex=2.0:98.0) 3.4 times the volume of the column was flowed to stabilize the column.

(2) The composition of the highly unsaturated fatty acid used as a raw material in this example is shown in the following Table 5. The highly unsaturated fatty acid in the raw material was subjected to ethyl esterification beforehand.

1.0 g of this raw material was dissolved in 2 ml of a mixed solvent (a volume ratio of IPE:n-Hex=2.0:98.0) and this solution was flowed into the column as prepared in (1).

First, the column was developed by 118 ml of the mixed solvent at a linear velocity of 1.0 cm/min, and the resultant effluent was condensed under reduced pressure in an evaporator, thus giving 0.29 g of oil as the first effluent fraction with the composition shown in the following Table 6.

Second, the column was developed by 23.6 ml of the mixed solvent at a linear velocity of 1.0 cm/min, and the resultant effluent was condensed under reduced pressure in an evaporator, thus giving 0.14 g of oil as the second effluent fraction with the composition shown in Table 6.

Third, the column was developed by 240.2 ml of the mixed solvent at a linear velocity of 1.0 cm/min, and the resultant effluent was condensed under reduced pressure in an evaporator, thus giving 0.48 g of oil as the third effluent fraction with the composition shown in Table 6.

Finally, the column was developed by 78.5 ml of acetone at a linear velocity of 1.0 cm/min, and the resultant effluent was condensed under reduced pressure in an evaporator, thus giving 0.03 g of oil as the fourth effluent fraction with the composition shown in Table 6.

0.48 g of the oil obtained as the third effluent fraction was further subjected to high-vacuum precision distillation using a packed column type precision distillation tower having a theoretical plate number of 8 under the conditions: a degree of vacuum of not more than 0.02 mm Hg at the top of the tower, a degree of vacuum of not more than 2.0 mm Hg at the bottom of the tower and an average distillation temperature of 165–210° C. 0.40 g of oil having the composition shown in Table 7 was obtained.

The composition of the fatty acids in the raw material used in Example 2 is shown in Table 5.

TABLE 5

| | Content of ethyl ester of each fatty acid (%) | | | |
|---|---|---|---|---|
| | ETA | EPA | DHA | Others |
| Raw material | 2.76 | 48.74 | 8.86 | 39.64 |

As a result of the chromatography in Example 2, the yield and the composition of each effluent fraction are shown in Table 6.

TABLE 6

| | | Content of ethyl ester of each fatty acid (%) | | | |
|---|---|---|---|---|---|
| | Yield (%) | ETA | EPA | DHA | Others |
| First effluent fraction | 29.0 | 0.06 | 0.0 | 0.0 | 99.94 |
| Second effluent fraction | 13.5 | 15.3 | 31.76 | 12.35 | 40.59 |
| Third effluent fraction | 48.0 | 0.92 | 77.68 | 12.28 | 9.12 |
| Fourth effluent fraction | 2.5 | 0.0 | 2.73 | 0.0 | 97.27 |

The yield and the composition of the oil obtained by distillation of the third effluent fraction in Example 2 are shown in Table 7.

TABLE 7

| | | Content of ethyl ester of each fatty acid (%) | | | |
|---|---|---|---|---|---|
| | Yield (%) | ETA | EPA | DHA | Others |
| Product purified by distillation | 83.3 | 1.28 | 98.35 | 0.0 | 0.37 |

The result in Example 2 shows that EPA, the content of which was relatively low in the raw material, was separated and purified effectively by the column chromatography of the present invention and that ETA or its ester was largely reduced. Further, EPA of high purity of 98% or more could be obtained in the subsequent purification process by distillation.

EXAMPLE 3

(1) 39.2 g of spherical silica gel having an average particle diameter of 60 micrometers (manufactured by Soken Chemical & Engineering Co., Ltd.) were slurried with acetone and this slurry was filled under pressure in a stainless steel medium pressure column (20 mm in inside diameter×250 mm in length). Then, a mixed solvent (a volume ratio of IPE:n-Hex=3.2:96.8) 4.2 times the volume of the column was flowed to stabilize the column.

(2) The composition of the highly unsaturated fatty acid used as a raw material in this example is shown in the following Table 8. The highly unsaturated fatty acid in the raw material was subjected to ethyl esterification beforehand.

2.0 g of this raw material was dissolved in 4 ml of the mixed solvent (a volume ratio of IPE:n-Hex=3.2:96.8) and this solution was flowed into the column as prepared in (1).

First, the column was developed by 220 ml of the mixed solvent at a linear velocity of 7.0 cm/min, and the resultant effluent was condensed under reduced pressure in an evaporator, thus giving 0.07 g of oil as the first effluent fraction with the composition shown in the following Table 9.

Second, the column was developed by 7.4 ml of the mixed solvent at a linear velocity of 7.0 cm/min, and the resultant effluent was condensed under reduced pressure in an evaporator, thus giving 0.19 g of oil as the second effluent fraction with the composition shown in Table 9.

Third, the column was developed by 322.6 ml of the mixed solvent at a linear velocity of 7.0 cm/min, and the resultant effluent was condensed under reduced pressure in an evaporator, thus giving 1.73 g of oil as the third effluent fraction with the composition shown in Table 9.

Finally, the column was developed by 154 ml of acetone at a linear velocity of 7.0 cm/min, and the resultant effluent was condensed under reduced pressure in an evaporator, thus giving 0.02 g of oil as the fourth effluent fraction with the composition shown in Table 9.

The composition of the fatty acids in the raw material used in Example 3 is shown in Table 8.

TABLE 8

| | Content of ethyl ester of each fatty acid (%) | | | |
|---|---|---|---|---|
| | ETA | EPA | DHA | Others |
| Raw material | 3.22 | 96.03 | 0.0 | 0.75 |

As a result of the chromatography in Example 3, the yield and the composition of each effluent fraction are shown in Table 9.

TABLE 9

| | | Content of ethyl ester of each fatty acid (%) | | | |
|---|---|---|---|---|---|
| | Yield (%) | ETA | EPA | DHA | Others |
| First effluent fraction | 3.4 | 49.85 | 37.84 | 0.0 | 12.31 |
| Second effluent fraction | 9.5 | 19.53 | 78.47 | 0.0 | 2.00 |
| Third effluent fraction | 86.6 | 0.62 | 98.85 | 0.0 | 0.53 |
| Fourth effluent fraction | 1.1 | 0.0 | 57.17 | 0.52 | 42.31 |

The result in Example 3 shows that EPA, the content of which was high in the raw material, was separated and purified effectively by the column chromatography of the present invention and that ETA or its ester was largely reduced. Further, EPA of high purity of 98% or more could be obtained in 85% or more yield.

EXAMPLE 4

(1) 39.2 g of spherical silica gel having an average particle diameter of 20 micrometers (manufactured by Soken Chemical & Engineering Co., Ltd.) were slurried with acetone and this slurry was filled under pressure in a stainless steel medium pressure column (20 mm in inside diameter×250 mm in length). Then, a mixed solvent (a volume ratio of IPE:n-Hex=3.2:96.8) 3.4 times the volume of column was flowed to stabilize the column.

(2) 2.0 g of the same raw material as used in Example 1 was dissolved in 4 ml of a mixed solvent (a volume ratio of IPE:n-Hex=3.2:96.8) and this solution was flowed into the column as prepared in (1).

First, the column was developed by 227.6 ml of the mixed solvent at a linear velocity of 10 cm/min, and the resultant effluent was condensed under reduced pressure in an evaporator, thus giving 0.10 g of oil as the first effluent fraction with the composition shown in the following Table 10.

Second, the column was developed by 7.8 ml of the mixed solvent at a linear velocity of 10 cm/min, and the resultant effluent was condensed under reduced pressure in an evaporator, thus giving 0.18 g of oil as the second effluent fraction with the composition shown in Table 10.

Third, the column was developed by 455.4 ml of the mixed solvent at a linear velocity of 10 cm/min, and the resultant effluent was condensed under reduced pressure in an evaporator, thus giving 1.59 g of oil as the third effluent fraction with the composition shown in Table 10.

Finally, the column was developed by 157 ml of acetone at a linear velocity of 10 cm/min, and the resultant effluent was condensed under reduced pressure in an evaporator, thus giving 0.05 g of oil as the fourth effluent fraction with the composition shown in Table 10.

1.59 g of the oil obtained as the third effluent fraction was further subjected to high-vacuum precision distillation using a packed column type precision distillation tower having a theoretical plate number of 8 under the conditions: a degree of vacuum of not more than 0.02 mm Hg at the top of the tower, a degree of vacuum of not more than 2.0 mm Hg at the bottom of the tower and an average distillation temperature of 165–210° C. 1.28 g of oil having the composition shown in Table 11 was obtained.

As a result of the chromatography in Example 4, the yield and the composition of each effluent fraction are shown in Table 10.

TABLE 10

|  | Yield (%) | Content of ethyl ester of each fatty acid (%) | | | |
| --- | --- | --- | --- | --- | --- |
|  |  | ETA | EPA | DHA | Others |
| First effluent fraction | 4.9 | 40.77 | 7.48 | 3.94 | 47.81 |
| Second effluent fraction | 9.2 | 23.84 | 41.58 | 15.85 | 18.73 |
| Third effluent fraction | 79.7 | 0.81 | 79.44 | 11.49 | 8.26 |
| Fourth effluent fraction | 2.4 | 0.00 | 13.60 | 2.31 | 84.09 |

The yield and the composition of the oil obtained by distillation of the third effluent fraction in Example 4 are shown in Table 11.

TABLE 11

|  | Yield % | Content of ethyl ester of each fatty acid (%) | | | |
| --- | --- | --- | --- | --- | --- |
|  |  | ETA | EPA | DHA | Others |
| Product purified by distillation | 80.5 | 1.32 | 98.29 | 0.0 | 0.39 |

The result in Example 4 shows that in the case where the linear velocity in the column was high, EPA was separated and purified effectively by the column chromatography of the present invention and that ETA or its ester was largely reduced. Further, EPA of high purity of 98% or more could be obtained in 80% or more yield in the subsequent purification process by distillation.

COMPARATIVE EXAMPLE 2

(1) 39.2 g of spherical silica gel having an average particle diameter of 20 micrometers (manufactured by Soken Chemical & Engineering Co., Ltd.) were slurried with acetone and this slurry was filled under pressure in the same medium pressure column (20 mm in inside diameter×250 mm in length) as used in Example 1. Then, a mixed solvent (a volume ratio of ethyl acetate:n-Hex=1.5:98.5) 3.4 times the volume of column was flowed to stabilize the column.
(2) 2.0 g of the same highly unsaturated fatty acid mixture as used in Example 1 was dissolved in 4 ml of a mixed solvent (a volume ratio of ethyl acetate:n-Hex=1.5:98.5) and this solution was flowed into the column as prepared in (1).

First, the column was developed by 78.6 ml of the mixed solvent at a linear velocity of 7.0 cm/min, and the resultant effluent was condensed under reduced pressure in an evaporator, thus giving 0.13 g of oil as the first effluent fraction with the composition shown in the following Table 12.

Second, the column was developed by 196.2 ml of the mixed solvent at a linear velocity of 7.0 cm/min, and the resultant effluent was condensed under reduced pressure in an evaporator, thus giving 1.16 g of oil as the second effluent fraction with the composition shown in Table 12.

Third, the column was developed by 94.2 ml of the mixed solvent at a linear velocity of 7.0 cm/min, and the resultant effluent was condensed under reduced pressure in an evaporator, thus giving 0.64 g of oil as the third effluent fraction with the composition shown in Table 12.

Finally, the column was developed by 651.6 ml of the mixed solvent and 157.0 ml of acetone at a linear velocity of 7.0 cm/min, and the resultant effluent was condensed under reduced pressure in an evaporator, thus giving 0.06 g of oil as the fourth effluent fraction with the composition shown in Table 12.

TABLE 12

|  | Yield % | Content of ethyl ester of each fatty acid (%) | | | |
| --- | --- | --- | --- | --- | --- |
|  |  | ETA | EPA | DHA | Others |
| First effluent fraction | 6.6 | 14.10 | 45.27 | 14.14 | 26.49 |
| Second effluent fraction | 57.9 | 5.36 | 73.03 | 11.22 | 10.39 |
| Third effluent fraction | 32.1 | 0.85 | 79.53 | 10.74 | 8.88 |
| Fourth effluent fraction | 2.8 | 0.00 | 18.13 | 3.15 | 78.72 |

The result in Comparative Example 2 shows that ETA or its ester was insufficiently separated by using ethyl acetate as an ester solvent in the mixed solvent as a developing solvent, and also that the yield of EPA in the third effluent fraction was extremely low. High-vacuum precision distillation of the third effluent fraction, however, could result in EPA of 98% or more purity.

As described above, the process of the present invention is characterized by using a medium pressure column filled with spherical silica gel having a particle diameter of 1–100 micrometers and developing the column by a mixed solvent with a volume ratio of n-Hex:IPE=90-99:10-1, preferably 95-99:5-1, by which EPA or its ester can be separated and purified effectively and also ETA or its ester can be removed selectively. According to the present process, EPA or its ester can be separated and purified at low cost by using only silica gel as a filler in the column. The process can largely reduce initial and running costs for the separation and purification of EPA or its ester on an industrial scale.

Obviously, additional modifications and variations of the present invention are possible in light of the above teachings. It is therefore to be understood that within the scope of the appended claims, the invention may be practiced otherwise than as specifically described herein.

What is claimed is:
1. A process for separating and purifying eicosapentaenoic acid or its ester from a mixture containing a highly unsaturated fatty acid or its ester, which comprises developing the mixture containing the highly unsaturated fatty acid or its ester by a mixed solvent of an ether solvent and a hydrocarbon solvent, using a column filled with a silica gel having a particle diameter of 1 to 100 micrometers.

2. The process of claim 1 wherein the ether solvent is a dialkyl ether and the hydrocarbon solvent is an alkane hydrocarbon of 5–8 carbons.

3. The process of claim 1 wherein the mixed solvent is developed at a linear velocity of 1–10 cm/min in the column.

4. The process of claim 1 wherein a precision distillation is carried out after the development by the mixed solvent.

* * * * *

UNITED STATES PATENT AND TRADEMARK OFFICE
CERTIFICATE OF CORRECTION

PATENT NO.   : 6,433,201 B2
DATED        : August 13, 2002
INVENTOR(S)  : Fujita et al.

It is certified that error appears in the above-identified patent and that said Letters Patent is hereby corrected as shown below:

Title page,
Item [73], Assignee, should read:

-- [73]  Assignee: Nisshin Pharma Inc., Tokyo (JP) --

Signed and Sealed this

Twentieth Day of May, 2003

JAMES E. ROGAN
*Director of the United States Patent and Trademark Office*